(12) United States Patent
Bae et al.

(10) Patent No.: US 8,293,189 B2
(45) Date of Patent: Oct. 23, 2012

(54) TEST STRIP DESIGNED TO IMPROVE SPREADABILITY OF BLOOD

(75) Inventors: Byeong-Woo Bae, Anyang (KR);
Sung-Dong Lee, Anyang (KR);
Byung-Hoon Kho, Seongnam (KR);
Ji-Eon Ryu, Anyang (KR); Jin-Kyeong Kim, Gunpo (KR); Hyou-Arm Joung, Uiwang (KR)

(73) Assignee: Infopia Co., Ltd. (KR)

( * ) Notice: Subject to any disclaimer, the term of this patent is extended or adjusted under 35 U.S.C. 154(b) by 152 days.

(21) Appl. No.: 12/722,183

(22) Filed: Mar. 11, 2010

(65) Prior Publication Data

US 2010/0311154 A1    Dec. 9, 2010

(30) Foreign Application Priority Data

Jun. 4, 2009 (KR) .................. 10-2009-0049647

(51) Int. Cl.
*G01N 31/22* (2006.01)
(52) U.S. Cl. ....................................... 422/420
(58) Field of Classification Search .................. 422/420
See application file for complete search history.

(56) References Cited

U.S. PATENT DOCUMENTS

| | | |
|---|---|---|
| 5,135,716 A | 8/1992 | Thakore |
| 5,418,142 A | 5/1995 | Kiser et al. |
| 5,597,532 A | 1/1997 | Connolly |
| 5,786,164 A | 7/1998 | Rittersdorf et al. |
| 5,846,837 A | 12/1998 | Thym et al. |
| 6,036,919 A | 3/2000 | Thym et al. |
| 6,962,819 B1 * | 11/2005 | Kitajima ....................... 436/170 |
| 7,083,939 B2 | 8/2006 | Shull et al. |
| 7,087,397 B2 * | 8/2006 | Anaokar et al. ................ 435/11 |
| RE39,915 E | 11/2007 | Rittersdorf et al. |
| 7,435,577 B2 * | 10/2008 | Lawrence et al. .......... 435/287.7 |
| 7,560,288 B2 | 7/2009 | Carroll et al. |
| 2006/0063267 A1 | 3/2006 | Lawrence et al. |

FOREIGN PATENT DOCUMENTS

| | | |
|---|---|---|
| JP | 1997-503581 | 4/1997 |
| JP | 1999-508693 | 7/1999 |
| KR | 1020040013003 A | 11/2004 |
| KR | 1020060064807 | 6/2006 |

OTHER PUBLICATIONS

International Search Report for Application No. PCT/KR2010/002598 dated Nov. 29, 2010.

* cited by examiner

*Primary Examiner* — Bobby Ramdhanie
(74) *Attorney, Agent, or Firm* — Cantor Colburn LLP

(57) ABSTRACT

Disclosed is a test strip for measuring medical data, in which a hydrophilic material is introduced to improve the spreadability of blood. Having the structure comprising a blood-filtering layer designed to filter off either or both of erythrocytes and low-density lipoprotein (LDL) cholesterol from an applied blood sample; a reaction layer in which the blood sample free of erythrocytes and/or low-density lipoprotein (LDL) cholesterol is reacted with an reagent, and a hydrophilic material, intercalated between the blood-filtering layer and the reaction layer, for uniformly spreading the blood sample filtered through the filtering layer, the blood-filtering layer and the reaction layer being stacked between the lower support and the upper cover, the test strip prevents the infiltration of erythrocytes into the reaction layer and improves the spreadability of blood to reduce measurement errors, thus bringing about higher reproducibility.

5 Claims, 3 Drawing Sheets

TEST STRIP DESIGNED TO IMPROVE SPREADABILITY OF BLOOD

BACKGROUND OF THE INVENTION

1. Field of the Invention

The present invention relates to the measurement of medical data. More particularly, the present invention relates to a test strip for measuring medical data from blood.

2. Description of the Related Art

The total cholesterol level in blood, plasma or serum is known as one type of medical data indicative of the risk of coronary arteriosclerosis. However, since recent clinical studies have shown a positive correlation between the level of low-density lipoprotein (LDL) cholesterol and the risk of coronary arteriosclerosis, LDL cholesterol levels are preferred as a medical indicator to total cholesterol levels.

LDL cholesterol levels can be measured using test strips in which suitable reactive agents are contained. Most of the measurement strips have a structure in which a plurality of pads containing reagents therein are stacked between an upper cover and a lower support. This stack structure is designed to flow a sample vertically, and comprises a blood-filtering layer and a color-developing membrane. This conventional structure is disadvantageous in that there is a large deviation in the smoothness of the contact surface between an upper and a lower layer. In this case, blood, which reaching the pads, differs in spreadability from one region to another, giving rise to measurement errors. Therefore, conventional test strips do not guarantee the reproducibility of medical data using even the same samples.

SUMMARY OF THE INVENTION

Accordingly, the present invention has been made keeping in mind the above problems occurring in the prior art, and an object of the present invention is to provide a test strip which can measure medical data with reliability.

In order to accomplish the object, the present invention provides a test strip for measuring medical data in association with a measuring apparatus, comprising: an upper cover having one or more application holes; a lower support having one or more detected parts at positions corresponding to detecting units of the measuring apparatus; a blood-filtering layer designed to filter off either erythrocytes and/or low-density lipoprotein (LDL) cholesterol from an applied blood sample; a reaction layer in which the blood sample free of erythrocytes and/or low-density lipoprotein (LDL) cholesterol is reacted with an reagent; and a hydrophilic material, intercalated between the blood-filtering layer and the reaction layer, for uniformly spreading the blood sample filtered through the filtering layer, the blood-filtering layer and the reaction layer being stacked between the lower support and the upper cover.

Having the structure in which a hydrophilic material is introduced, the test strip in accordance with the present invention prevents the infiltration of erythrocytes into the reaction layer and improves the spreadability of blood to reduce measurement errors, thus bringing about higher reproducibility.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
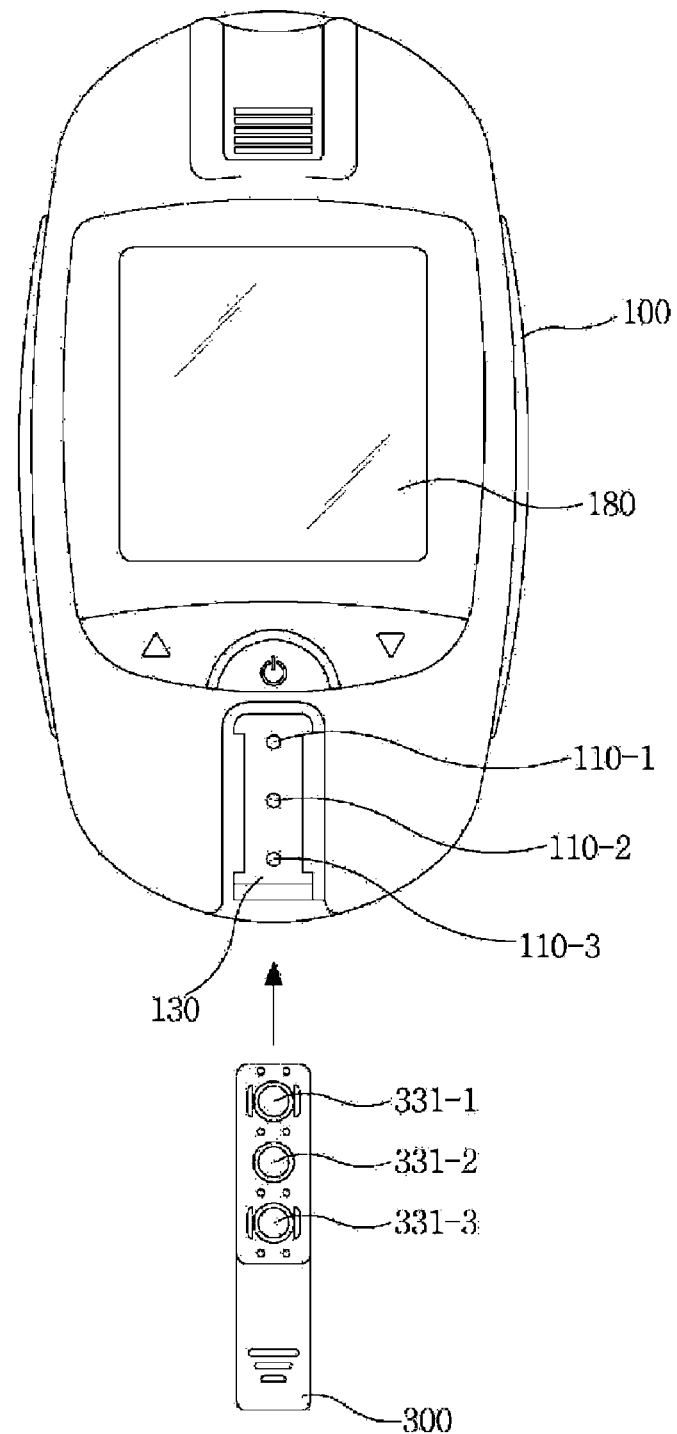
FIG. 1 is a schematic view showing an apparatus for measuring medical data and a test strip designed to be used in association therewith.

Reference now should be made to the drawings, in which the same reference numerals are used throughout the different drawings to designate the same or similar components.

FIG. 1 schematically shows an apparatus and a test strip for measuring medical data in accordance with an embodiment of the present invention. As seen in the schematic view of FIG. 1, the test strip 300 comprises a plurality of reaction regions 330 in which medical data, such as blood triglyceride and cholesterol levels, can be measured. The reaction regions 330 may differ in test target according to the positions thereof. For instance, the test strip of FIG. 1 has three reaction regions adapted for measuring levels of total cholesterol, high-density lipoprotein (HDL) cholesterol and triglyceride, respectively, all of which are used to quantitatively analyze low-density lipoprotein cholesterol levels. The apparatus 100 for measuring medical data comprises a power button, an integrated strip adaptor 130, and a display 180. The strip adaptor 130 is provided with a plurality of spaced detecting units on the mid line thereof. The detecting units 110 are designed to correspond respectively to the reaction regions 330 of the test strip 300. Depending on test types, a part or all of the detecting units 110 are activated to detect reactions occurring in the reaction regions 330.

Figure 2:
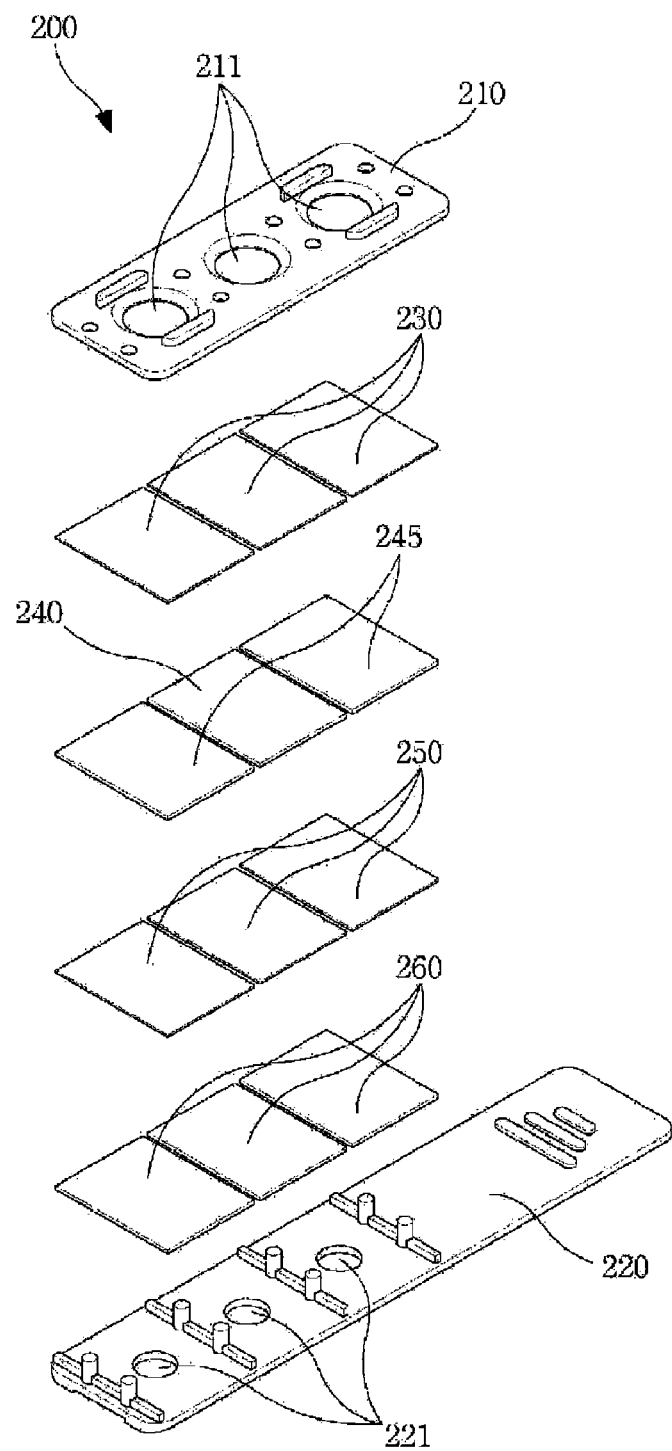
FIG. 2 is an exploded perspective view showing a test strip according to an embodiment of the present invention.

With reference to FIG. 2, a test strip 200 in accordance with an embodiment of the present invention is shown in an exploded perspective view. As seen in this exploded perspective view of FIG. 2, the test strip 200 comprises an upper cover 210 with a plurality of application holes 211 constructed therein, a middle structure separable into many stacked layers, and a lower support 220.

The upper cover 210 has one or more application holes 211 through which the user can load blood samples on the test strip and which may differ in measurement target from one to another. For example, the upper cover 210 has three application holes 211 to determine blood low-density lipoprotein cholesterol levels.

On the lower support 220, detected parts 221 are located at positions corresponding to the detecting units 110 of the strip adaptor 130 in the apparatus 100. The apparatus 100 determines medical data through the detected parts 221.

The middle structure comprises a blood-spreading layer 230, a blood-filtering layer, a hydrophilic material 250, and a reaction layer 260. The blood-filtering layer is sectioned into an erythrocyte and low-density lipoprotein (LDL) cholesterol-filtering zone 240 and erythrocyte-filtering zones 245. The erythrocyte and low-density lipoprotein (LDL) cholesterol-filtering zone is located beneath the second application hole which targets high-density lipoprotein cholesterol (HDL) while the other regions account for the erythrocyte-filtering zones 245.

Constructed with a porous polyester mesh, a woven fabric such as a cotton fabric or gauze, the blood-spreading zone 230 mainly functions to spread the blood thereover quickly and uniformly.

The erythrocyte and low-density lipoprotein (LDL) cholesterol-filtering zone 240 is comprised of a glass fiber pad containing a hemagglutinating agent and an LDL cholesterol precipitating agent. The glass fiber pad ranges in diameter from 0.5 to 2 microns, and is 0.25~0.40 mm, and preferably 0.37 mm in length. Both the hemagglutinating agent and the precipitating agent are uniformly distributed in an impregnated or fixed form over the pad. The precipitating agent useful in the present invention may be lectin, a cation polymer and/or a saccharide. Examples of the lectin include PHA (phytohemagglutinin), concanavalin A, PWM (pokeweed mitogen) and wheat-germ agglutinin. Among the cationic polymers is poly(diallyldimethylammonium chloride). The saccharides useful in the present invention may be mono-, di- and/or polysaccharides, such as sorbitol, sugar, oligosaccharides, etc. Functioning to selectively precipitate LDL cholesterol in blood, the precipitating agent useful in the present invention may be selected from among sulfonated polysaccharides, heparin, phosphotungstic acid (PTA), dextran sulfate, and salts of Group II cations therewith.

The erythrocyte filtering zone is composed of a glass fiber pad containing a hemagglutinating agent. Among the hemagglutinating agents useful in the present invention, as mentioned above, is lectin, a cationic polymer or a saccharide. Examples of the lectin include PHA (phytohemagglutinin), concanavalin A, PWM (pokeweed mitogen) and wheat-germ agglutinin. Of the cationic polymer is representative poly(diallyldimethylammonium chloride). The saccharides useful in the present invention may be mono-, di- and/or polysaccharides. When the blood, after passing through the blood spreading layer 230, reaches the pad, the erythrocytes thereof are agglutinated by the hematogglutinating agent. The agglutinated erythrocytes cannot be transmitted to the reaction layer 260.

The term "hydrophilic material," as used herein, is intended to refer to a material which has an oxygen atom or a hydroxy radical at the terminal group or functional group thereof, such as polyvinylpyrrolidone (PVP), polyvinylalcohol (PVA) or polyethanol glycol (PEG), thereby allowing hydrophilic treatment. Located between the blood filtering layer and the reaction layer 260, the hydrophilic material 250 functions to prevent the penetration of the erythrocytes unfiltered by the blood filtering layer into the reaction layer 260 and to spread the filtered blood.

In one preferred embodiment of the present invention, the hydrophilic material 250 may be in the form of a hydrophilized porous mesh. The mesh may have a pore size of from 1 to 500 μm and a thickness of 1 μm or less and may be composed of polyester. The porous mesh may be hydrophilized by reacting with a hydrophilic compound such as polyvinylpyrrolidone (PVP), polyvinylalcohol (PVA) or polyethylene glycol (PEG), or by introducing an oxygen atom or a hydroxy radical into the terminal group or functional group thereof.

In a preferred embodiment of the present invention, the hydrophilic material 250 may be applied in the form of gel, powder or film to the reaction layer 260 or the blood filtering layer. When the hydrophilic material 250 is applied in the form of gel, both or either of the reaction layer 260 and the blood filtering layer may be coated physically with the hydrophilic material 250 or it may be printed on the pad. For application in the form of powder, microparticles of the hydrophilic material are sprayed on the reaction layer 260 or the blood filtering layer to form a rough surface which is effective for uniformly absorbing the filtered blood. In the case of the film form, a film made of the hydrophilic material is inserted between the reaction layer and blood filtering layer, like the porous mesh.

In order to obtain medical data, the reaction layer 260 is designed to react with the blood from which erythrocytes and LDL cholesterol are removed. The reaction layer contains a reagent which can react with the erythrocyte- and LDL cholesterol-free blood. The reagent may be impregnated or fixed into the pad. In a preferred embodiment of the present invention, high-density lipoprotein (HDL) cholesterol is quantitatively analyzed. In this case, HDL cholesterol is cleaved into free cholesterol and fatty acid by cholesterol esterase and the free cholesterol is reacted with oxygen in the presence of cholesterol oxidase to form hydrogen peroxide which undergoes a color reaction with a coloring reagent in the presence of peroxidase.

Figure 3:
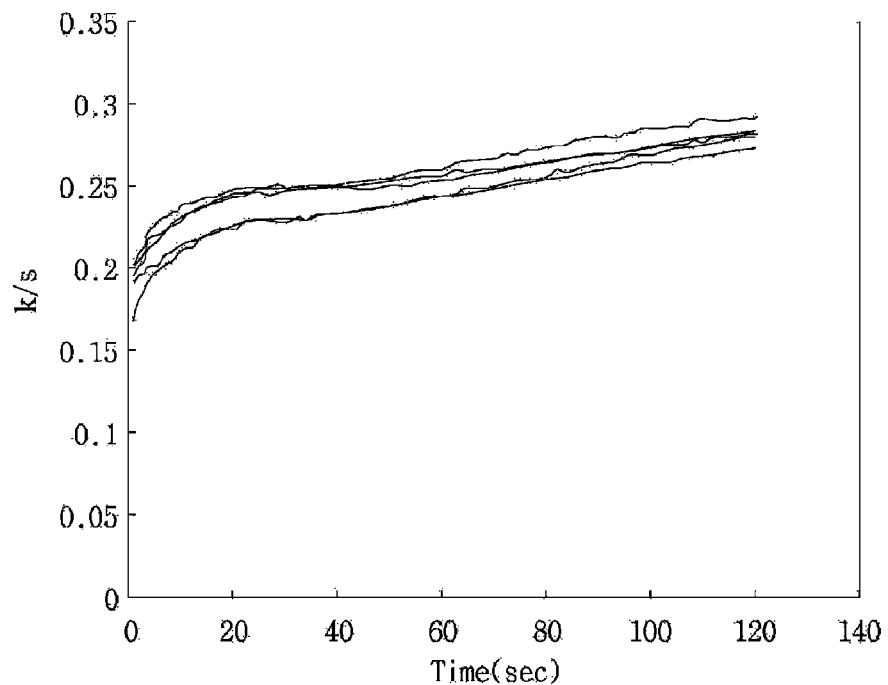
FIG. 3 is a graph showing the reflectance (k/s) obtained with a conventional test strip.
Figure 4:
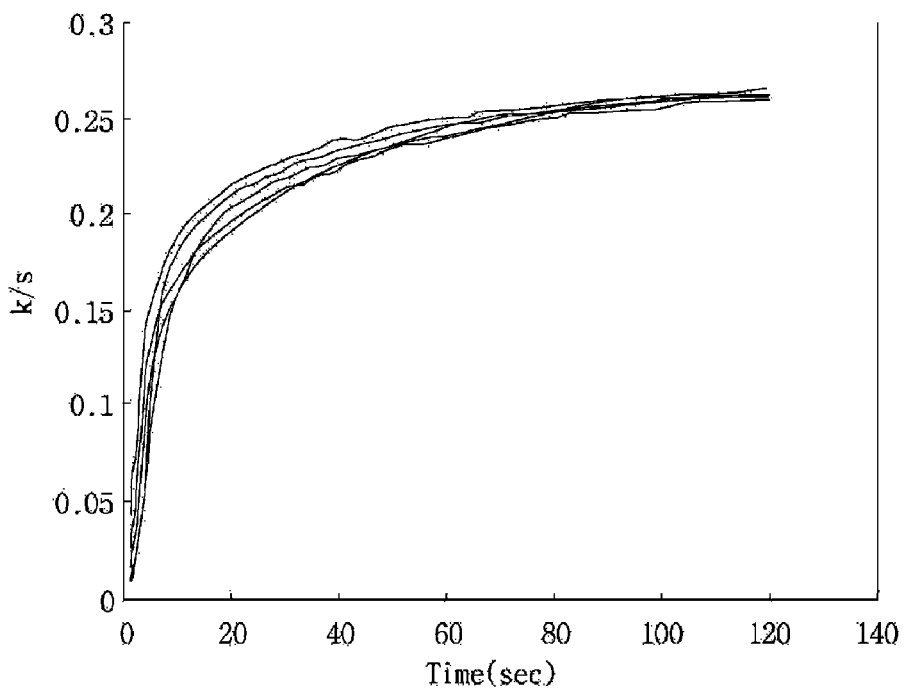
FIG. 4 is a graph showing the reflectance (k/s) obtained with a test strip of the present invention under the same condition.

FIGS. 3 and 4 are reflectance graphs obtained with a conventional test strip and a test strip according to the present invention under the same condition, respectively.

In FIGS. 3 and 4, reflectance (k/s) is plotted five times against time, with the same blood loaded onto the strips. The plot pattern of FIG. 4 is observed to stably converge compared to that of FIG. 3. At the point of 90 sec, the conventional test strip showed a mean reaction value of 29.7 with a coefficient of variation of 4.3% while the test strip of the present invention showed a mean reaction value of 27.2 with a coefficient of variation of 2.6%. A lower coefficient of variation accounts for higher reproducibility with the same sample. Accordingly, the test strip of the present invention is better in reproducibility than is the conventional test strip.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A test strip for measuring medical data in association with a measuring apparatus, comprising:
    an upper cover having three application holes;
    a lower support having three detected parts at positions corresponding to detecting units of the measuring apparatus;
    a blood-filtering layer comprising:
        an erythrocyte and low-density lipoprotein (LDL) cholesterol-filtering zone located beneath a middle application hole of the three application holes and designed to filter off both of erythrocytes and low-density lipoprotein (LDL) cholesterol from an applied blood sample; and
        an erythrocyte filtering zone designed to filter off erythrocytes from the applied blood sample;

a reaction layer in which the blood sample free of erythrocytes and low-density lipoprotein (LDL) cholesterol from the blood-filtering layer is reacted with an reagent; and a hydrophilic material of a hydrophilized porous mesh, intercalated between the blood-filtering layer and the reaction layer, for uniformly spreading the blood sample filtered through the filtering layer, the blood-filtering layer and the reaction layer being stacked between the lower support and the upper cover.

2. The test strip according to claim 1, wherein the porous mesh ranges in pore size from 1 to 500 μm.

3. The test strip according to claim 1, wherein the hydrophilic material is applied to either or both of the reaction layer and the blood-filtering layer.

4. The test strip according to claim 3, wherein the hydrophilic material is applied in a form of gel, powder, or film.

5. The test strip according to claim 1, wherein the hydrophilic material is selected from among polyvinylpyrrolidone (PVP), polyvinyl alcohol (PVA) and polyethylene glycol (PEG).

* * * * *